United States Patent [19]

Dumoulin et al.

[11] Patent Number: 5,445,150
[45] Date of Patent: Aug. 29, 1995

[54] INVASIVE SYSTEM EMPLOYING A RADIOFREQUENCY TRACKING SYSTEM

[75] Inventors: Charles L. Dumoulin, Ballston Lake; Robert D. Darrow, Scotia, both of N.Y.

[73] Assignee: General Electric Company, Schenectady, N.Y.

[21] Appl. No.: 10,720

[22] Filed: Jan. 29, 1993

Related U.S. Application Data

[63] Continuation-in-part of Ser. No. 793,962, Nov. 18, 1991, abandoned.

[51] Int. Cl.$^6$ ............................................. A61B 5/00
[52] U.S. Cl. .................................. 128/653.1; 128/899; 340/825.36; 340/825.49
[58] Field of Search ................... 128/653.1, 897, 898, 128/899, 903; 607/154, 156; 250/216, 221; 340/825.36, 825.49

[56] References Cited

U.S. PATENT DOCUMENTS

| | | | |
|---|---|---|---|
| 4,173,228 | 11/1979 | Van Steenwyk et al. | 128/653.1 |
| 4,905,698 | 3/1990 | Strohl, Jr. et al. | 128/737 |
| 4,994,665 | 2/1991 | Wernsing | 128/775 |
| 5,005,592 | 4/1991 | Cartmell | 128/899 |
| 5,042,486 | 8/1991 | Pfeiler et al. | 128/653.1 |
| 5,099,845 | 3/1992 | Besz et al. | 128/653.1 |
| 5,105,829 | 4/1992 | Fabian et al. | 128/899 |
| 5,107,862 | 4/1992 | Fabian et al. | 128/899 |
| 5,211,165 | 5/1993 | Dumoulin et al. | 128/899 |
| 5,252,962 | 10/1993 | Urbas et al. | 128/903 |
| 5,255,680 | 10/1993 | Darrow et al. | 128/653.1 |
| 5,265,610 | 11/1993 | Darrow et al. | 128/899 |
| 5,271,400 | 12/1993 | Dumoulin et al. | 128/899 |

Primary Examiner—Krista M. Pfaffle
Attorney, Agent, or Firm—Lawrence P. Zale; Marvin Snyder

[57] ABSTRACT

An invasive imaging system employs a self-contained RF transmitter attached to an invasive device which allows tracking of the invasive device within a subject without physical connections to a tracking/display system and without the use of ionizing rays. An imaging system obtains a medical diagnostic image of the subject. The self-contained RF transmitter is comprised of a power generator, a power conversion means such as an oscillator which converts the generated power to a radiofrequency (RF) signal, and a broadcasting means such as a tuned transmit coil for radiating the RF signal. The radiated RF signal is received by receive coils of a tracking/display means which calculates the location of the RF transmitter. The tracking/display means displays the medical diagnostic image on a monitor and superimposes a symbol on the image at a position corresponding to the calculated location of the RF transmitter. Prior to operation, the power generator may be energized inductively, photo-voltaically, or by direct contact with either an external power supply. The power generator may also be a charged battery sealed inside the RF transmitter. The RF transmitter may be implanted to track the motion of internal tissues.

4 Claims, 7 Drawing Sheets

INVASIVE SYSTEM EMPLOYING A RADIOFREQUENCY TRACKING SYSTEM

This application is a continuation-in-part of Ser. No. 07/793,962, filed Nov. 18, 1991, now abandoned.

CROSS-REFERENCE TO RELATED APPLICATIONS

This application is related to applications "TRACKING SYSTEM TO FOLLOW THE POSITION AND ORIENTATION OF A DEVICE WITH RADIOFREQUENCY FIELDS", Ser. No. 08/091,419 now U.S. Pat. No. 5,577,678; "TRACKING SYSTEM TO FOLLOW THE POSITION AND ORIENTATION OF A DEVICE WITH RADIOFREQUENCY FIELD GRADIENTS", Ser. No. 07/753,565 now U.S. Pat. No. 5,211,165; "STEREOSCOPIC X-RAY FLUOROSCOPY SYSTEM USING RADIOFREQUENCY FIELDS", Ser. No. 07/753,564 now U.S. Pat. No. 5,251,635; "AUTOMATIC GANTRY POSITIONING FOR IMAGING SYSTEMS", Ser. No. 07/753,567 now U.S. Pat. No. 5,255,680; and MULTI-PLANAR X-RAY FLUOROSCOPY SYSTEM USING RADIOFREQUENCY FIELDS, Ser. No. 07/753,566 now U.S. Pat. No. 5,265,610, all by Charles Lucian Dumoulin, all filed on Sep. 3, 1991 and all assigned to the present assignee. This application is also related to application "INDUCTIVELY COUPLED DEVICES FOR USE IN RF TRACKING SYSTEMS", Ser. No. 07/793,923 now abandoned, filed simultaneously with the parent application of this application and assigned to the present assignee.

BACKGROUND OF THE INVENTION

1. Field of the Invention

The present invention relates to medical procedures in which an invasive device is inserted into a living body, and more particularly concerns the tracking of such a device with the use of radiofrequency fields.

2. Description of Related Art

X-ray fluoroscopes are used routinely to monitor the placement of invasive devices during diagnostic and therapeutic medical procedures. Conventional X-ray fluoroscopes are designed to minimize X-ray dosage. Nevertheless, some procedures can be very long and the accumulated X-ray dose to the patient can become significant. The long term exposure of the attending medical staff is of even greater concern since they participate in these procedures regularly. This is also a problem with other types of ionizing radiation such as positron emission tomography (PET), gamma ray camera and computed axial tomography (CAT) procedures. Consequently, it is desirable to reduce the overall ionizing radiation dose to all persons during these procedures.

Methods to track invasive devices without the use of X-rays have been disclosed previously in the aforementioned patent applications Ser. No. 07/753,563 and Ser. No. 07/753,565 hereby incorporated by reference. These applications describe systems in which an invasive device incorporating a radiofrequency coil is placed within a living body and its position is followed by either detecting or broadcasting a radiofrequency (RF) signal.

While systems employing invasive RF devices which must be plugged into a control unit to be tracked are feasible, it would be more desirable to have a system which employs invasive devices that do not require physical connection to the control unit while being tracked.

SUMMARY OF THE INVENTION

An invasive system for performing invasive procedures within a subject incorporates a self-contained radiofrequency (RF) transmitter which is tracked by an external RF tracking means. The RF transmitter can be either built into an invasive device, or attached to the device prior to insertion into a subject. The RF transmitter contains a power generation means, an a power conversion means such as an RF oscillator and a broadcasting means such as a transmitting. Coil all hermetically sealed in a non-bioreactive case. The power generation means may be charged inductively, photo-voltaically, or by direct contact with an external power supply prior to being inserted into the subject. Alternatively, a battery can be sealed into the invasive device in a charged state. The power generation means drives the RF oscillator which in turn excites-the transmitting coil. The transmitting coil creates a dipole field which is detected by an external tracking means, which determines the instantaneous location of the invasive device within the subject. A medical imaging means creates an image of the subject. A display means displays the image and superimposes upon it a symbol representing the RF transmitter at a position corresponding to its location within the subject. The RF transmitter is interactively tracked through the subject without requiring other medical diagnostic images.

OBJECTS OF THE INVENTION

It is an object of the present invention to provide interactive images of a self-contained RF transmitter during an invasive procedure.

It is another object of the present invention to provide interactive images of a self-contained RF transmitter during an invasive procedure without the need for external power wires leading to the RF transmitter during the procedure.

It is another object of the present invention to image internal tissue motion.

BRIEF DESCRIPTION OF THE DRAWINGS

The features of the invention believed to be novel are set forth with particularity in the appended claims. The invention itself, however, both as to organization and method of operation, together With further objects and advantages thereof, may best be understood by reference to the following description taken in conjunction with the accompanying drawing in which:

DETAILED DESCRIPTION OF THE INVENTION

Figure 1:
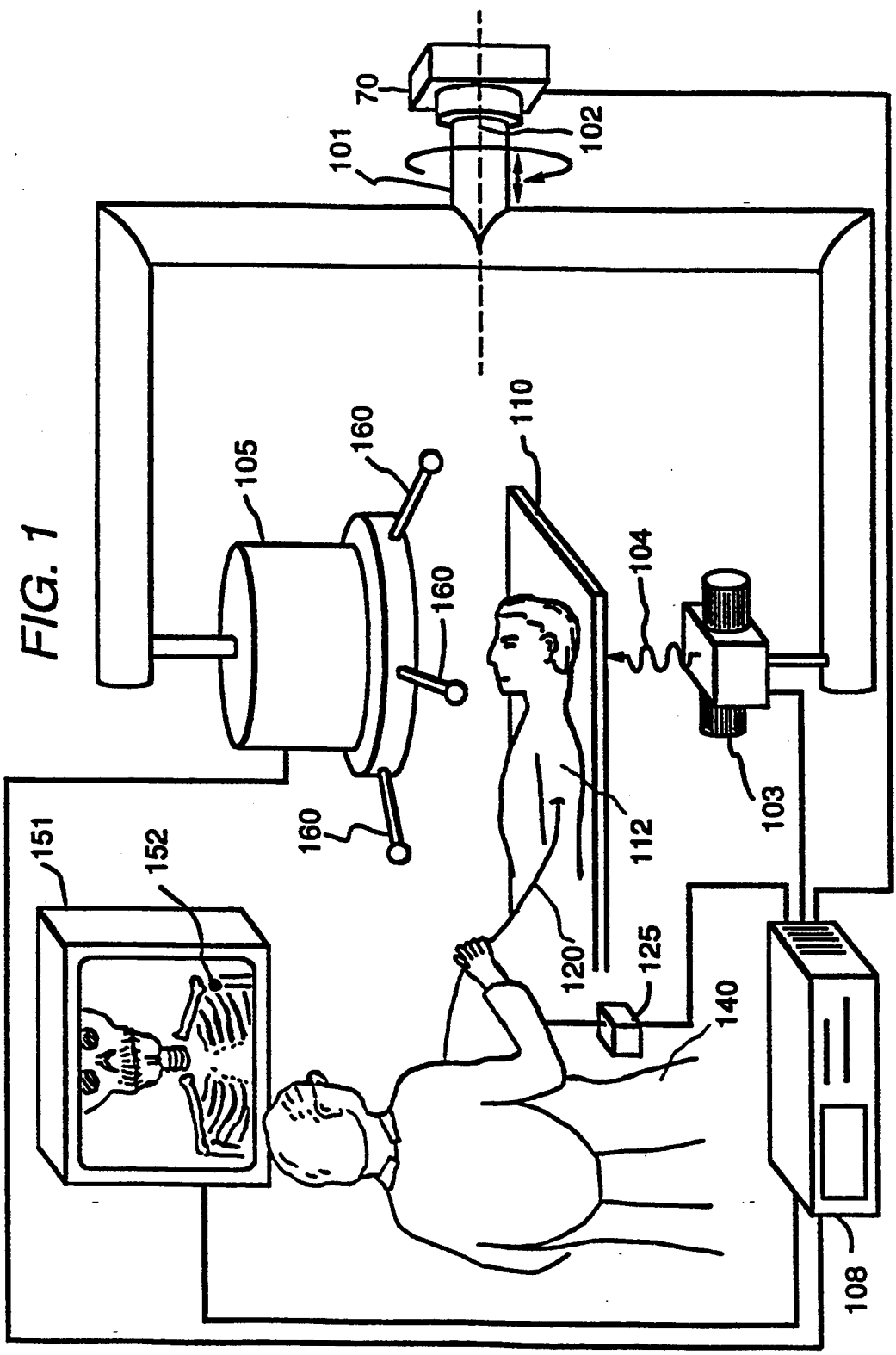
FIG. 1 is a part perspective and part schematic view of one embodiment of the present invention in use during an invasive procedure.
Figure 6:
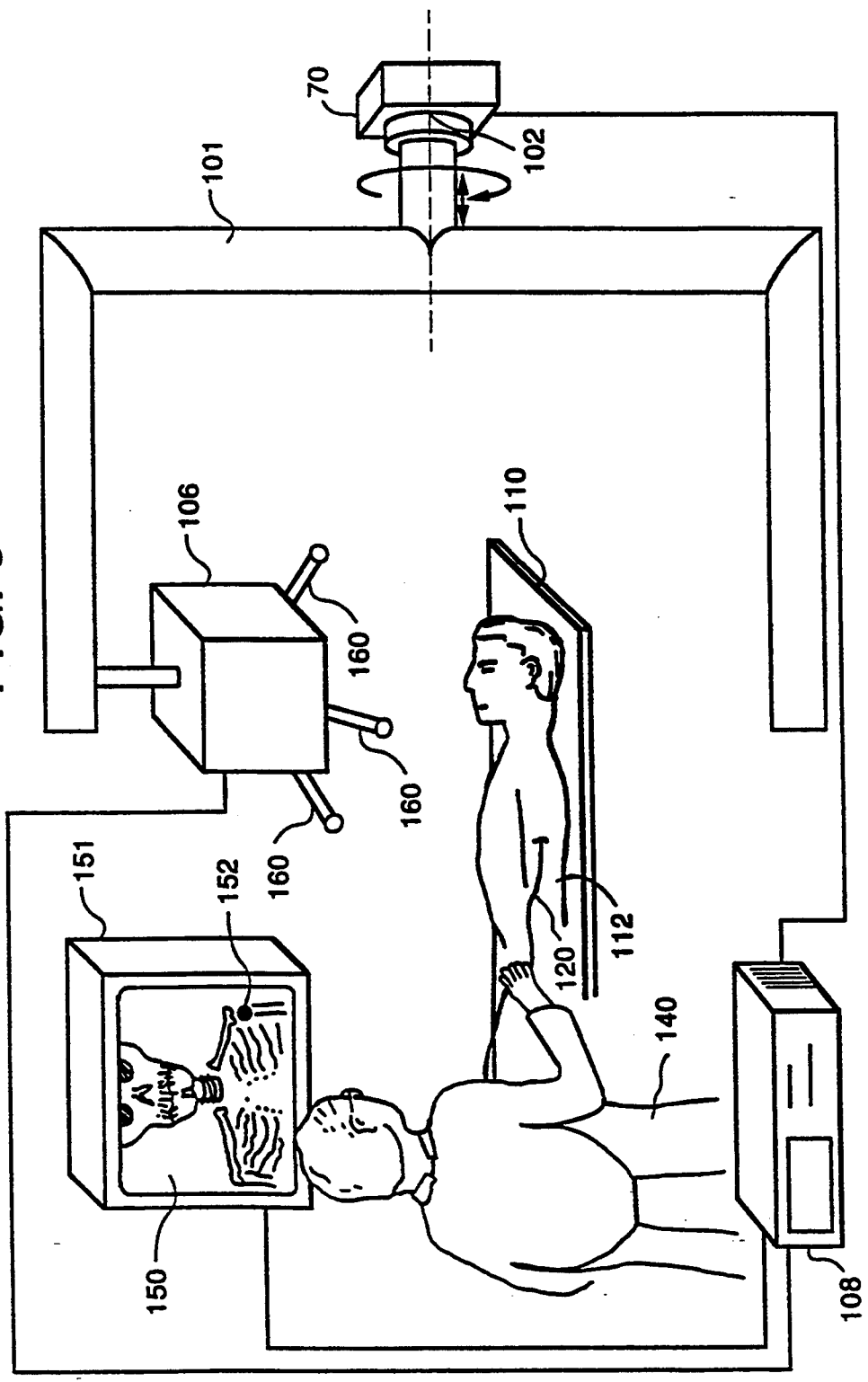
FIG. 6 is part perspective and part schematic view of one embodiment of the present invention in use during an invasive procedure employing alternate medical imaging means such as a gamma camera or an ultrasound imaging system.
Figure 7:
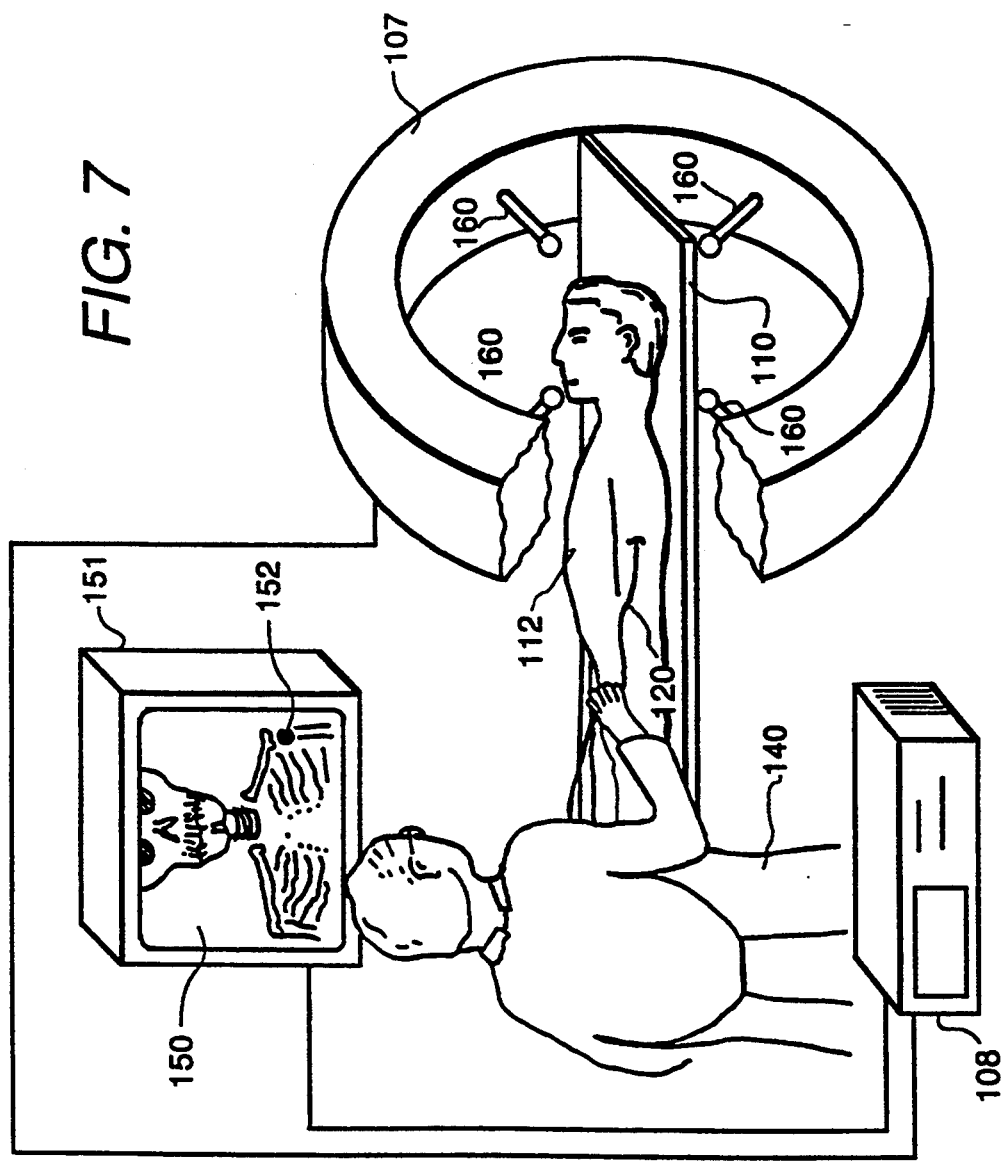
FIG. 7 is part perspective and part schematic view of one embodiment of the present invention in use during an invasive procedure employing alternate medical imaging means such as a computed axial tomography (CAT) or an positron emission tomography (PET) imaging system.

In FIG. 1, an invasive device 120 having a self-contained RF transmitter attached to its end is shown being introduced into a living subject 112 and tracked as described in aforementioned U.S. patent applications Ser. Nos. 07/753,563 and 07/753,565. A support arm 101, capable of being rotated about at least one axis 102 and translated by a gantry control means 70, is provided in order to hold a medical imaging source such as X-ray source 103 that emits a substantially collimated beam of X-rays 104 suitable for X-ray imaging and X-ray fluoroscopy. Support arm 101 also holds an X-ray detection means 105 aligned with the propagation direction of X-rays 104 emitted by an X-ray source 103. X-rays 104 penetrate a subject Support table 110 and subject 112. FIG. 1 illustrates an X-ray imaging system, but in alternate embodiments any medical imaging means which provides an image of the subject may be employed. Medical imaging means 106 of FIG. 6 may be a gamma camera or ultrasound imaging system. Alternatively medical imaging means 107 of FIG. 7 may be a positron emission tomography (PET), and computed axial tomography (CAT) imaging means. These will apply equally to the present invention but, for simplicity, the remainder of the application will describe only X-ray imaging.

According to the previously disclosed inventions, a plurality of M RF receive coils 160 are placed about the subject. In the embodiment illustrated in FIG. 1, receive coils 160 are attached to X-ray detection means 105.

An invasive device 120 incorporating at least one self-contained. RF transmitter (not shown) at an end which also includes a transmit coil is positioned inside the subject by an operator 140. The invasive device 120 is shown entering the left arm of the subject. Transmit coils may be attached to several invasive devices, if several such devices are employed in the medical procedure, with at least one transmit coil per invasive device.

Each invasive device 120 creates a dipole electromagnetic field which is detected by RF receive coils 160. The signals detected by receive coils 160 are used by a tracking/display unit 108 described in detail in the aforementioned patent applications Ser. Nos. 07/753,563 and 07/753,565 to calculate the position and orientation of the transmit coil (and therefore the end of invasive device 120). The calculated position of invasive device 120 is displayed by superposition of a symbol 152 on an X-ray image appearing on display monitor 151. Video monitor 151 is driven by tracking/display unit 108. The instantaneous location of invasive device 120 is updated several times per second (ideally 12 to 60 times per second) and provides an approximation of the fluoroscopic image of invasive device 120 that the operator would expect to see with a conventional X-ray fluoroscopic system. Following the preferred procedure, the operator initiates acquisition of X-ray image only when it is deemed necessary, in order to minimize X-ray dose to the subject and the operator.

Figure 2:
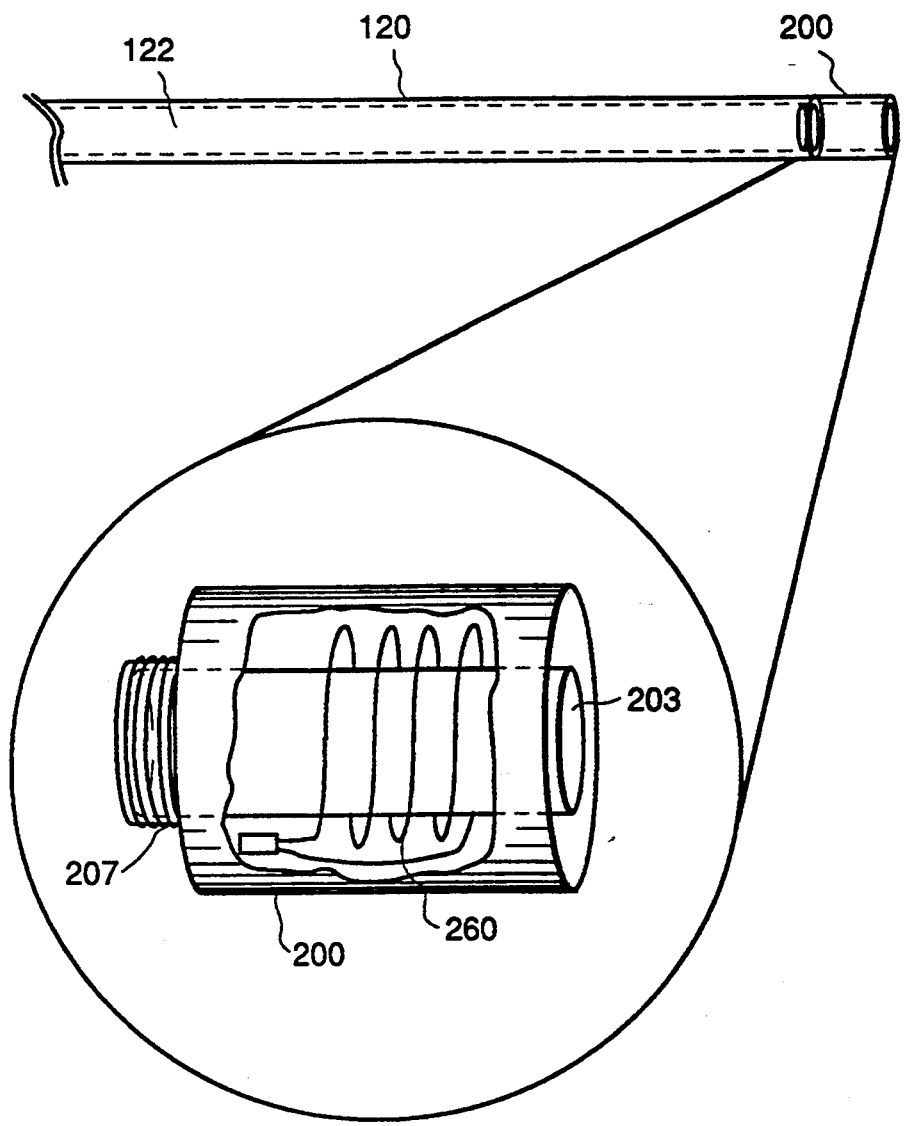
FIG. 2 is an illustration of the connection of the RF transmitter of the present invention to an invasive device.

FIG. 2 shows an invasive device 120, such as a catheter, attached to an one embodiment 200 of the RF transmitter of the present invention. Assembly 200 is attached to invasive device 120 by a threaded means at the end to be inserted into a living body. The center 122 of invasive device 120 is hollow to allow the passage of other surgical equipment through its center acting as a guide. Assembly 200 also has an open center 203 to allow passage of equipment. A transmit coil 260 can be seen inside RF transmitter 200 that wraps around center opening 203. Here the axis of coil 260 coincides with the axis of center opening 203.

Figure 3:
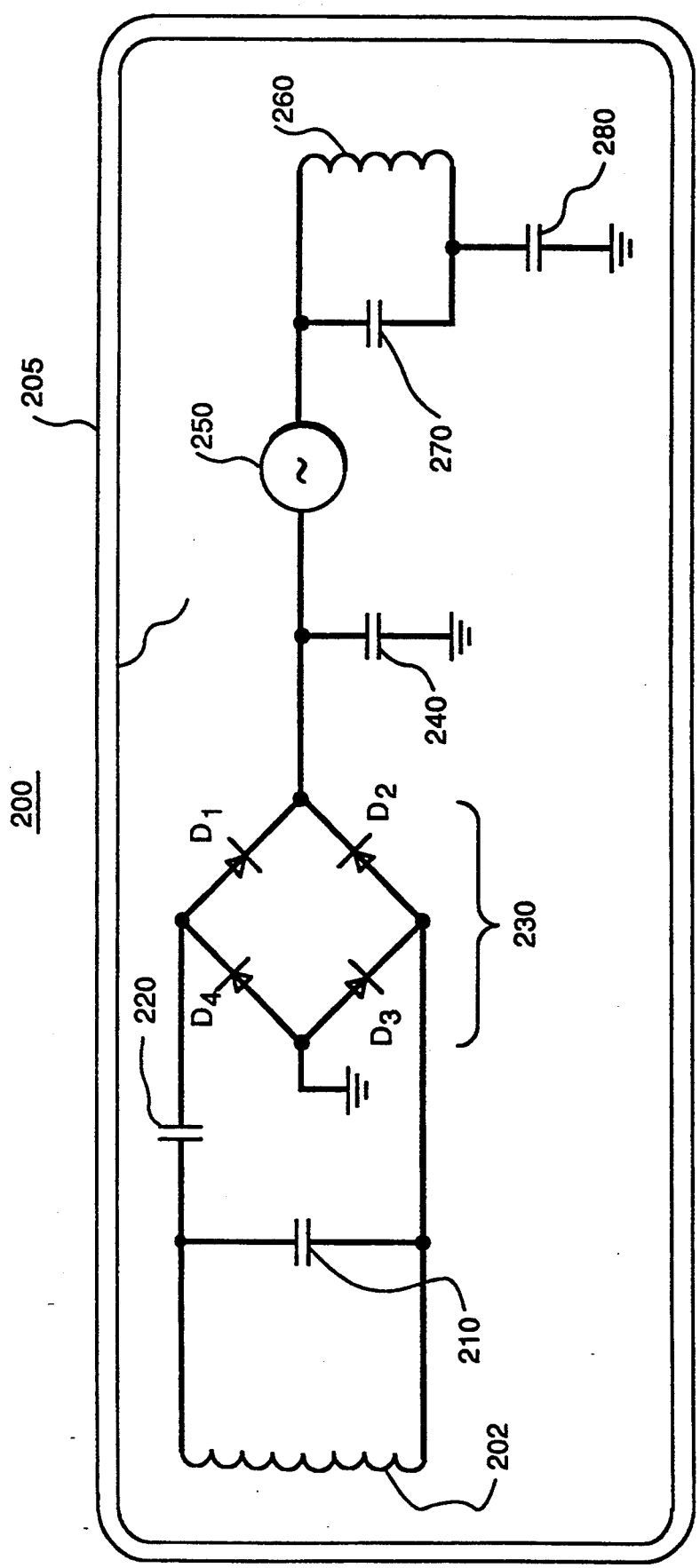
FIG. 3 is a schematic diagram illustrating a first embodiment of the present invention which relates to an inductively powered RF transmitter.

A first embodiment 200 of a self-contained RF transmitter is shown in greater detail in FIG. 3. This RF transmitter is comprised of a receiver coil 202 which is tuned by its inductance and the capacitance of a parallel-coupled capacitor 210 to a selected radiofrequency. This radiofrequency is chosen to be outside the bandwidth used by the tracking system to calculate the position of RF transmitter 200. Energy at this frequency is introduced into the subject by the external continuous wave transmitter (not shown). Inductive coupling between an external continuous wave transmitter and coil 202 is used to provide energy to RF transmitter 200. The signal detected by coil 202 passes through a series-Connected matching capacitor 220 to a rectifying means 230, here shown as a full wave bridge comprising four diodes $D_1$, $D_2$, $D_3$, $D_4$. Other rectifying means may be employed in the alternative, such as a half-wave bridge. The rectified signal is smoothed with a filter means 240, shown here as a capacitor coupled across the output of bridge 230, and is passed to an RF oscillator means 250. The oscillator converts the rectified signal to a second radiofrequency which is within the bandwidth used by receive coils 160 (FIG. 1) and passed to tracking display unit 108 (FIG. 1). The second radiofrequency Signal is propagated to a transmit coil 260 which is tuned and matched with a parallel capacitor 270 and a series capacitor 280. The signal broadcast by transmit coil 260 is detected by receive coils 160 (FIG. 1) and passed to tracking/display unit 108 (FIG. 1). The transmitted signal is not phase locked with the tracking/display unit, so that phase-locked loop, 125 of FIG. 1, must be connected to, or must be incorporated into the tracking/display unit. Since RF transmitter 200 is to be inserted within a subject, the RF transmitter 200 is hermetically sealed in a case 205 comprised of non-bioreactive materials Such as teflon.

Figure 4:
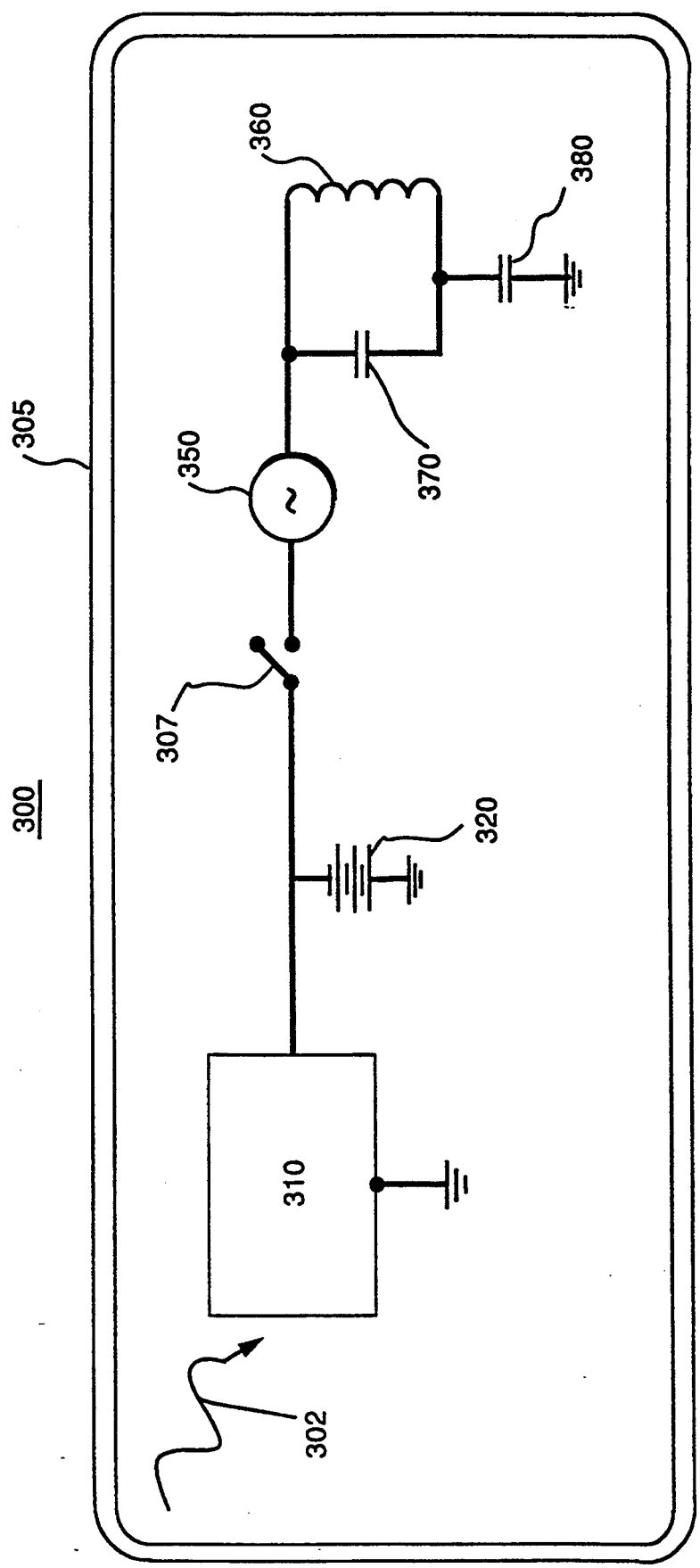
FIG. 4 is a schematic diagram illustrating a second embodiment of the present invention which relates to a photo-voltaically powered RF transmitter.

A second embodiment 300 of the self-contained RF transmitter is shown in FIG. 4. Here light 302 at a suitable wavelength shines through non-bioreactive case 305 onto a photovoltaic device 310 situated therein to generate a DC electrical current. Case 305 may have a transparent window, or be made of transparent material such as quartz. The generated DC current charges a battery 320 connected to device 310 to store energy. An RF oscillator 350 in series with photo-voltaic device 310 draws energy from battery 320 to create a radiofrequency signal. The capacity of the battery is chosen to be sufficient to drive oscillator 350 for the time that the RF transmitter is in use within the subject. The radiofrequency signal generated by oscillator 350 is conducted in series to a transmit coil 360 which radiates radiofrequency energy and which is tuned and matched to the desired radiofrequency by a parallel capacitor 370 and a series capacitor 380. A switching means 307 may be employed in series with photo-voltaic device 310 and oscillator 350 to permit the RF transmitter to be charged at the time of manufacture, rather than immediately before use.

Figure 5:
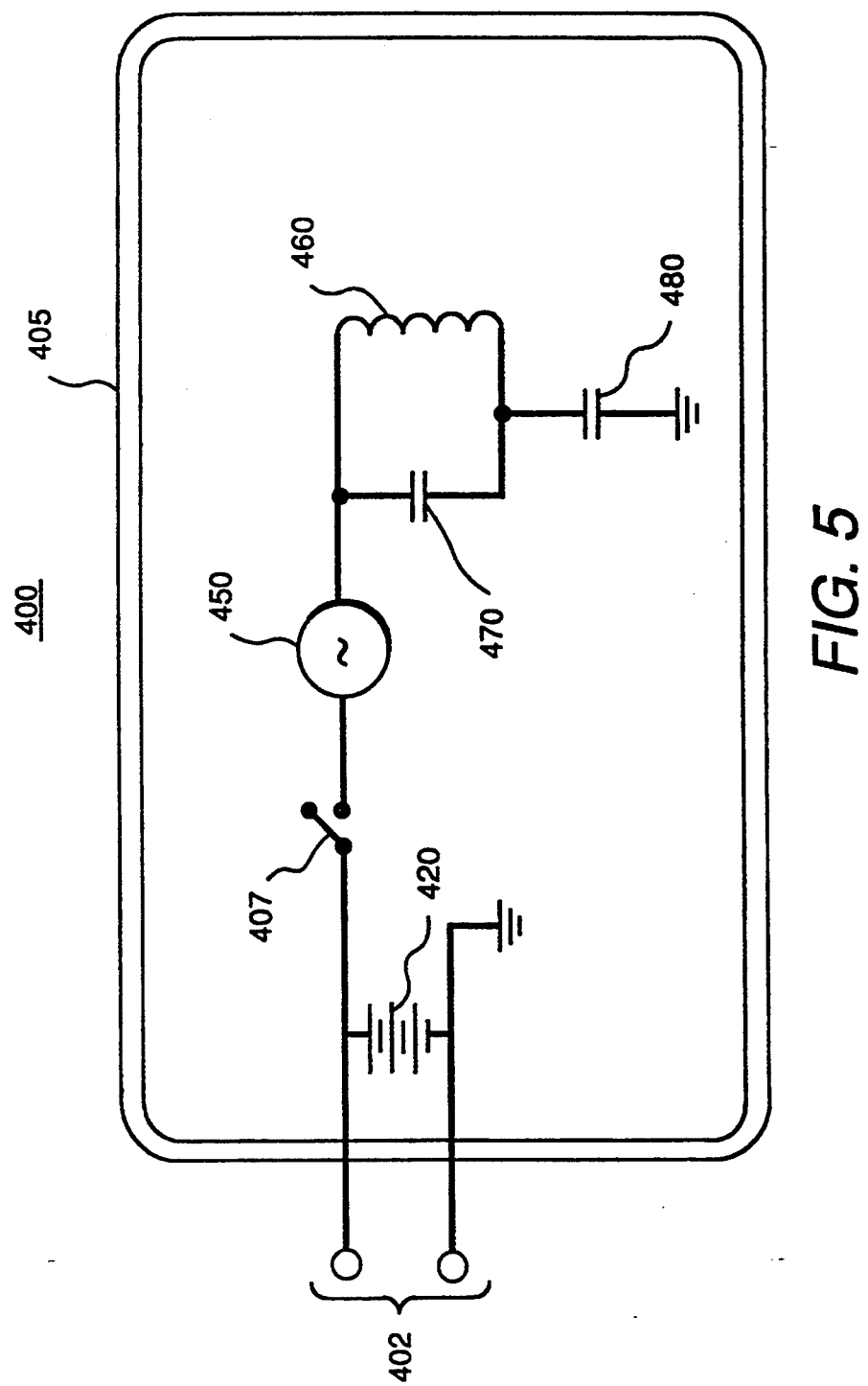
FIG. 5 is a schematic diagram illustrating a third embodiment of the present invention which relates to a battery powered RF transmitter.

A third embodiment 400 of the self-contained RF transmitter is shown in FIG. 5. Here a direct physical connection 402 extends through a non-bioreactive case 405, and allows connection to an external power supply (not shown) to charge a battery 420 in parallel. Battery 420 in turn drives RF oscillator 450. As in the embodiment of FIG. 4., the capacity of battery 420 is chosen to be sufficient to drive-the oscillator for the time that the RF transmitter is in use within the subject. The radiofrequency signal generated by oscillator 450 is conducted in series to a transmit coil 460 which is tuned and matched to the desired radiofrequency by a parallel capacitor 470 and a series capacitor 480. A switching means 407 may be employed in the same manner, and to perform a similar function, as switching means 307 in the embodiment of FIG. 4.

The self-contained invasive assemblies of the present invention can be used with invasive devices as described above or they can be used advantageously as implants. Implants incorporating the invasive assemblies of the present invention can be placed Within the heart wall during surgery. Motion of the myocardium can then be monitored without X-rays whenever needed.

Self-contained invasive assemblies can be incorporated into any device which is to be followed with an RF tracking system. These include, but are not limited to biopsy needles, endoscopes, laparoscopes, catheters, guide wires, surgical devices, therapeutic devices and three-dimensional pointing devices. In the embodiments of the current invention employing an energy storage device, the device maybe either a capacitor or a battery.

While several presently preferred embodiments of the novel self-contained RF invasive devices have been described in detail herein, many modifications and variations will now become apparent to those skilled in the art. It is, therefore, to be understood that the appended claims are intended to cover all such modifications and variations as fall within the true spirit of the invention.

What is claimed is:

1. A invasive imaging system to provide interactive images during an invasive procedure of a subject, comprising:
   a) a imaging means for providing an image of said subject;
   b) an invasive device adapted to be inserted into said subject;
   c) a self-contained radiofrequency (RF) transmitter attached to the invasive device, the self-contained RF transmitter including:
      i. power conversion means for converting electrical power into a RF signal at a selected frequency,
      ii. power generation means for providing electrical power to the power conversion means comprising an RF coil coupled to receive RF power from an external source during operation, and a rectification means coupled to the RF coil for rectifying the received RF power into electrical power and providing the electrical power to the power conversion means,
      iii. broadcasting means for broadcasting the RF signal so as to create a dipole magnetic field, and
      iv. hermetically sealed case constructed from non-bioreactive materials encasing the power conversion means, power generation means and broadcasting means having a size and shape allowing it to move freely within said patient;
   d) a plurality of receive coils placed at a plurality of known locations for receiving the broadcasted RF signal; and
   e) external RF tracking/display means employing a phase-locked loop for synchronizing the external RF tracking/display means with the RF transmitter, the external RF tracking/display means coupled to the receive coils and responsive to the RF signal for determining a location and orientation of the RF transmitter based upon strength and phase of the broadcasted RF signal received at the receive coils, and for displaying the image of the subject and a symbol on the image at a position corresponding to the location of the RF transmitter in the subject.

2. The invasive imaging system of claim 1 wherein the invasive device comprises one of the group consisting of a guide wire, a catheter, an endoscope, a laparoscope, a biopsy needle, a surgical tool and a therapeutic device.

3. The invasive imaging system of claim 1 wherein the hermetically sealed case has a size and shape allowing it to be surgically implanted and tracked as it passes through said body by the external RF tracking/display means.

4. The invasive imaging system of claim 1 wherein the imaging means comprises one of the group consisting of positron emission tomography (PET) imaging means, gamma ray camera, and computed axial tomography (CAT) imaging means.

* * * * *